United States Patent
Xu

(10) Patent No.: US 11,904,022 B2
(45) Date of Patent: Feb. 20, 2024

(54) CARRIER-FREE CURCUMIN NANOPARTICLE FOR EGFR POSITIVE CANCER THERAPY

(71) Applicant: University of South Carolina, Columbia, SC (US)

(72) Inventor: Peisheng Xu, Chapin, SC (US)

(73) Assignee: UNIVERSITY OF SOUTH CAROLINA, Columbia, SC (US)

( * ) Notice: Subject to any disclaimer, the term of this patent is extended or adjusted under 35 U.S.C. 154(b) by 72 days.

(21) Appl. No.: 17/213,750

(22) Filed: Mar. 26, 2021

(65) Prior Publication Data
US 2021/0369861 A1 Dec. 2, 2021

Related U.S. Application Data

(60) Provisional application No. 63/029,782, filed on May 26, 2020.

(51) Int. Cl.
| | |
|---|---|
| A61K 47/69 | (2017.01) |
| A61K 9/51 | (2006.01) |
| A61K 47/54 | (2017.01) |
| A61K 47/60 | (2017.01) |

(52) U.S. Cl.
CPC ........ *A61K 47/6935* (2017.08); *A61K 9/5123* (2013.01); *A61K 9/5146* (2013.01); *A61K 9/5192* (2013.01); *A61K 47/54* (2017.08); *A61K 47/60* (2017.08)

(58) Field of Classification Search
CPC ...... A61K 31/517; A61K 31/12; A61K 47/54; A61K 47/60; A61K 47/6935; A61K 9/5123; A61K 9/5146; A61K 9/5192
See application file for complete search history.

(56) References Cited

PUBLICATIONS

Cheng et al., "Carrier-Free Nanoassembly of Curcumin-Erlotinib Conjugate for Cancer Targeted Therapy," Advanced Healthcare Materials, vol. 9, No. 19 (Oct. 7, 2020).*
Gao et al., "Erlotinib-Guided Self-Assembled Trifunctional Click Nanotheranostics for Distinguishing Druggable Mutations and Synergistic Therapy of Nonsmall Cell Lung Cancer," Mol. Pharmaceutics 2018, 15, 11, 5146-5161.*
Chen et al., "Curcumin based combination therapy for anti-breast cancer: from in vitro drug screening to in vivo efficacy evaluation," Front. Chem. Sci. Eng. 10, 383-388 (2016). https://doi.org/10.1007/s11705-016-1574-2.*
Yamauchi et al., "Coadministration of Erlotinib and Curcumin Augmentatively Reduces Cell Viability in Lung Cancer Cells," Phytotherapy Research, vol. 28, No. 5 (May 2014), pp. 728-735.*
Javadi et al., "Curcumin mediated down-regulation of $\alpha V\beta 3$ integrin and up-regulation of pyruvate dehydrogenase kinase 4 (PDK4) in Erlotinib resistant SW480 colon cancer cells," Phytotherapy Research, vol. 32, No. 2, pp. 355-364 (Feb. 2018).*

* cited by examiner

*Primary Examiner* — Alicia L Otton
(74) *Attorney, Agent, or Firm* — DORITY & MANNING, P.A.

(57) ABSTRACT

A carrier-free nanoparticle based on the self-assembly of curcumin-erlotinib conjugate (EPC) that exhibits stronger cell killing, better anti-migration effects, and anti-invasion effects for pancreatic cancer cells than the combination of free curcumin and erlotinib.

1 Claim, 12 Drawing Sheets
Specification includes a Sequence Listing.

CARRIER-FREE CURCUMIN NANOPARTICLE FOR EGFR POSITIVE CANCER THERAPY

STATEMENT REGARDING FEDERALLY SPONSORED RESEARCH

This disclosure was made with government support under R15 CA188847 by the National Institute of Health. The government has certain rights in the invention.

TECHNICAL FIELD

The present disclosure relates to a carrier-free nanoparticle based on the self-assembly of curcumin-erlotinib conjugate (EPC) that exhibits stronger cell killing, better anti-migration effects, and anti-invasion effects for pancreatic cancer cells than the combination of free curcumin and erlotinib.

BACKGROUND

Epithelial cell cancers, for example, prostate cancer, breast cancer, colon cancer, lung cancer, pancreatic cancer, ovarian cancer, cancer of the spleen, testicular cancer, cancer of the thymus, etc., are diseases characterized by abnormal, accelerated growth of epithelial cells. This accelerated growth initially causes a tumor to form. Eventually, metastasis to different organ sites can also occur. Although progress has been made in the diagnosis and treatment of various cancers, these diseases still result in significant mortality.

Epidermal growth factor receptor (EGFR) is a 170 kilodalton (kDa) membrane-bound protein expressed on the surface of epithelial cells. EGFR is a member of the growth factor receptor family of protein tyrosine kinases, a class of cell cycle regulatory molecules. (W. J. Gullick et al., 1986, Cancer Res., 46:285-292). EGFR is activated when its ligand (either EGF or TGF-α) binds to the extracellular domain, resulting in autophosphorylation of the receptor's intracellular tyrosine kinase domain (S. Cohen et al., 1980, J. Biol. Chem., 255:4834-4842; A. B. Schreiber et al., 1983, J. Biol. Chem., 258:846-853).

EGFR is the protein product of a growth promoting oncogene, erbB or ErbB1, that is but one member of a family, i.e., the ERBB family of protooncogenes, believed to play pivotal roles in the development and progression of many human cancers. In particular, increased expression of EGFR has been observed in breast, bladder, lung, head, neck and stomach cancer as well as glioblastomas. The ERBB family of oncogenes encodes four, structurally-related transmembrane receptors, namely, EGFR, HER-2/neu (erbB2), HER-3 (erbB3) and HER-4 (erbB4). Clinically, ERBB oncogene amplification and/or receptor overexpression in tumors have been reported to correlate with disease recurrence and poor patient prognosis, as well as with responsiveness in therapy. (L. Harris et al., 1999, Int. J. Biol. Markers, 14:8-15; and J. Mendelsohn and J. Baselga, 2000, Oncogene, 19:6550-6565).

EGFR is composed of three principal domains, namely, the extracellular domain (ECD), which is glycosylated and contains the ligand-binding pocket with two cysteine-rich regions; a short transmembrane domain, and an intracellular domain that has intrinsic tyrosine kinase activity. The transmembrane region joins the ligand-binding domain to the intracellular domain. Amino acid and DNA sequence analysis, as well as studies of nonglycosylated forms of EGFR, indicate that the protein backbone of EGFR has a mass of 132 kDa, with 1186 amino acid residues (A. L. Ullrich et al., 1984, Nature, 307:418-425; J. Downward et al., 1984, Nature, 307:521-527; C. R: Carlin et al., 1986, Mol. Cell. Biol., 6:257-264; and F. L. V. Mayes and M. D. Waterfield, 1984, The EMBO J., 3:531-537).

The binding of EGF or TGF-α to EGFR activates a signal transduction pathway and results in cell proliferation. The dimerization, conformational changes and internalization of EGFR molecules function to transmit intracellular signals leading to cell growth regulation (G. Carpenter and S. Cohen, 1979, Ann. Rev. Biochem., 48:193-216). Genetic alterations that affect the regulation of growth factor receptor function, or lead to overexpression of receptor and/or ligand, result in cell proliferation. In addition, EGFR has been determined to play a role in cell differentiation, enhancement of cell motility, protein secretion, neovascularization, invasion, metastasis and resistance of cancer cells to chemotherapeutic agents and radiation. (M.-J. Oh et al., 2000, Clin. Cancer Res., 6:4760-4763).

A variety of inhibitors of EGFR have been identified, including a number already undergoing clinical trials for treatment of various cancers. For a recent summary, see de Bono, J. S. and Rowinsky, E. K. (2002), "The ErbB Receptor Family: A Therapeutic Target For Cancer", Trends in Molecular Medicine, 8, S 19-26.

Anti-cancer drug loaded nanoparticles have been explored extensively to decrease side effects while improving their therapeutic efficacy. Most nanoparticle based drug delivery systems are composed of a carrier and a payload. However, due to the low drug loading content, premature drug release, non-standardized or non-uniform carrier structure, and difficulty in predicating the fate of the carrier, only a few nanomedicines have been approved by FDA.

Accordingly, it is an object of the present disclosure to provide an improved nanoparticle with improved migration and invasion effects. Hereby, we developed a carrier-free nanoparticle based on the self-assembly of curcumin-erlotinib conjugate (EPC), which has a size of about 146.3 nm with a PDI of 0.157. The EPC nanoparticle exhibited stronger cell killing, better anti-migration and anti-invasion effects for BxPC-3 pancreatic cancer cells than the combination of free curcumin and erlotinib. Furthermore, EPC nanoparticle could effectively accumulate in the tumor tissue in a xenograft tumor mouse model. Consequently, EPC effectively reduced the growth of pancreatic tumor and extended the medium survival time of the tumor-bearing mice from 22 days to 68 days. In addition, no systemic toxicity was detected in the major organs from the mice receiving EPC treatment. Attributed to the uniformity of the curcumin-erlotinib conjugate and easiness of scaling up. EPC could be translated into power tool in fighting against pancreatic cancer.

Citation or identification of any document in this application is not an admission that such a document is available as prior art to the present disclosure.

SUMMARY

The above objectives are accomplished according to the present disclosure by providing in a first embodiment, a method for preparing a carrier-free nanoparticle for tumor growth inhibition. The method may include synthesizing PEG modified erlotinib, conjugating the PEG modified erlotinib with curcumin to form an erlotinib-curcumin conjugate, dissolving the erlotinib-curcumin conjugate in acetone to form a solution, and adding the solution dropwise to deionized water to self-assemble at least one nanoparticle.

Further, the at least one nanoparticle may be administered to a cancer cell. Still, the cancer cell may be a pancreatic cancer cell. Further yet, the cancer cell is a human pancreatic cancer cell. Again, the nanoparticle may be delivered in a dose of at least 10 mg/kg into a subject. Further, the nanoparticle may be offered at a dose of 1 mg/kg, 2, 3, 4, 5, 6, 7, 8, 9, 10, 15, 20, 25, 30, 35, 40, 45, 50, or 55 mg/kg as well as ranges of these amounts. Still yet, introduction of the at least one nanoparticle may reduce cancer cell viability. Moreover, introduction of the at least one nanoparticle may slow tumor volume growth profiles.

In a further embodiment, a method for inhibiting tumor growth is provided. The method may include introducing a carrier-free nanoparticle to a tumor environment, wherein cancer cells uptake the carrier-free nanoparticle and introduction of the carrier-free nanoparticle may inhibit tumor growth. Still, the carrier-free nanoparticle may comprise a erlotinib-curcumin conjugate. Further, the erlotinib-curcumin conjugate comprises a PEG linked erlotinib-curcumin conjugate. Again, the tumor environment may comprise a pancreatic cancer tumor. Yet again, the carrier-free nanoparticle decreases $\alpha v \beta 33$ integrin expression and increases PDK4 gene expression. Further yet, the carrier-free nanoparticle article may be delivered in a dose of at least 10 mg/kg into a subject. Further, the nanoparticle may be offered at a dose of 1 mg/kg, 2, 3, 4, 5, 6, 7, 8, 9, 10, 15, 20, 25, 30, 35, 40, 45, 50, or 55 mg/kg as well as ranges of these amounts.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present disclosure will be obtained by reference to the following detailed description that sets forth illustrative embodiments, in which the principles of the disclosure may be utilized, and the accompanying drawings of which.

Figure 1:
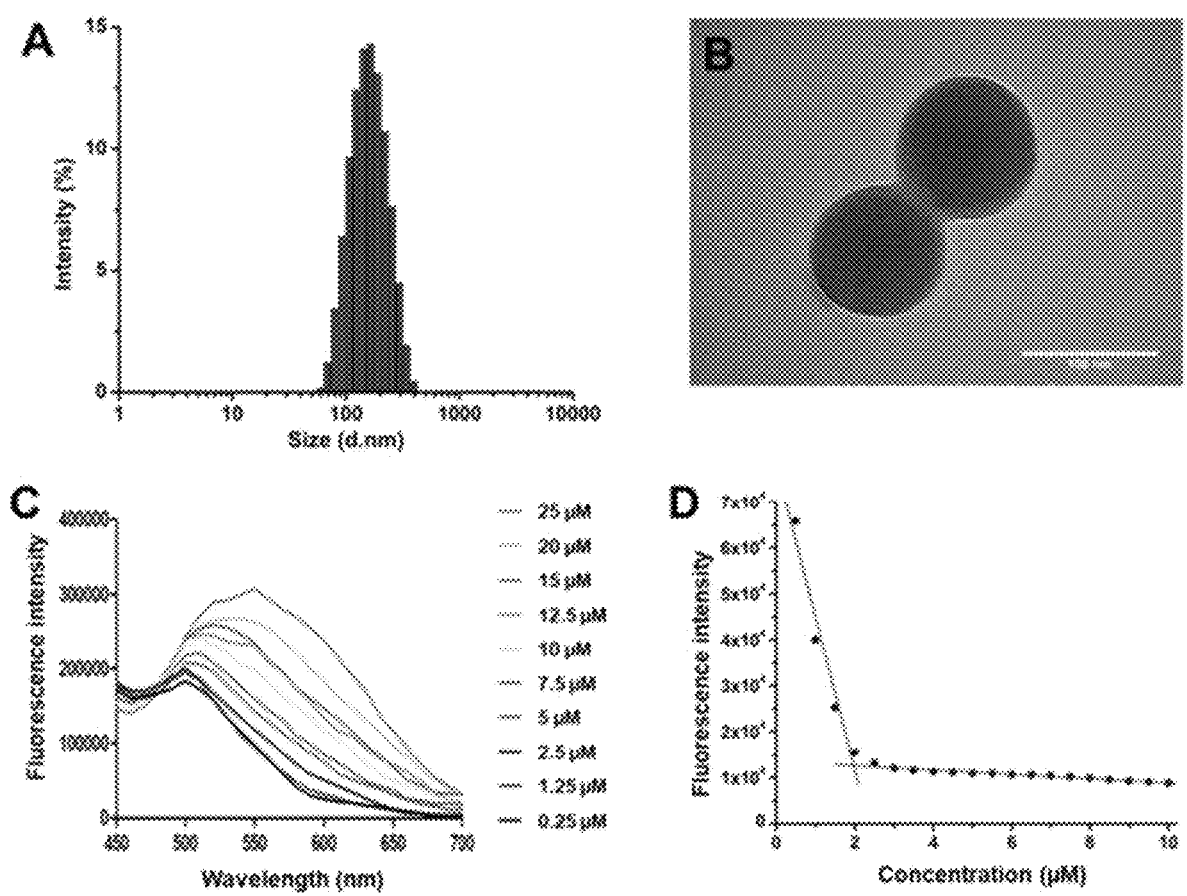
FIG. 1 shows size distribution at (A), TEM image at (B), fluorescence spectra at (C), and CMC determination at (D) of an EPC nanoparticle article of the current disclosure.

The figures herein are for illustrative purposes only and are not necessarily drawn to scale.

DETAILED DESCRIPTION OF A PREFERRED EMBODIMENT

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further embodiment includes from the one particular value and/or to the other particular value. The recitation of numerical ranges by endpoints includes all numbers and fractions subsumed within the respective ranges, as well as the recited endpoints. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes I X, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

As used herein, "about," "approximately," "substantially," and the like, when used in connection with a measurable variable such as a parameter, an amount, a temporal duration, and the like, are meant to encompass variations of and from the specified value including those within experimental error (which can be determined by e.g. given data set, art accepted standard, and/or with e.g. a given confidence interval (e.g. 90%, 95%, or more confidence interval from the mean), such as variations of +/−10% or less, +/−5% or less, +/−1% or less, and +/−0.1% or less of and from the specified value, insofar such variations are appropriate to perform in the disclosure. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, a "biological sample" may contain whole cells and/or live cells and/or cell debris. The biological sample may contain (or be derived from) a "bodily fluid". The present disclosure encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, and cell cultures from bodily fluids. Bodily fluids may be obtained from a mammal organism, for example by puncture, or other collecting or sampling procedures.

As used herein, "agent" refers to any substance, compound, molecule, and the like, which can be administered to a subject on a subject to which it is administered to. An agent can be inert. An agent can be an active agent. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

As used herein, "active agent" or "active ingredient" refers to a substance, compound, or molecule, which is biologically active or otherwise that induces a biological or physiological effect on a subject to which it is administered to. In other words, "active agent" or "active ingredient" refers to a component or components of a composition to which the whole or part of the effect of the composition is attributed.

As used herein, "administering" refers to any suitable administration for the agent(s) being delivered and/or subject receiving said agent(s) and can be oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition to the perivascular space and adventitia. For example, a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration routes can be, for instance, auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratym panic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes, which typically depends on the disease to be treated, subject being treated, and/or agent(s) being administered.

As used herein "cancer" can refer to one or more types of cancer including, but not limited to, acute lymphoblastic leukemia, acute myeloid leukemia, adrenocortical carcinoma, Kaposi Sarcoma, AIDS-related lymphoma, primary central nervous system (CNS) lymphoma, anal cancer, appendix cancer, astrocytomas, atypical teratoid/Rhabdoid tumors, basa cell carcinoma of the skin, bile duct cancer, bladder cancer, bone cancer (including but not limited to Ewing Sarcoma, osteosarcomas, and malignant fibrous histiocytoma), brain tumors, breast cancer, bronchial tumors, Burkitt lymphoma, carcinoid tumor, cardiac tumors, germ cell tumors, embryonal tumors, cervical cancer, cholangiocarcinoma, chordoma, chronic lymphocytic leukemia, chronic myelogenous leukemia, chronic myeloproliferative neoplasms, colorectal cancer, craniopharyngioma, cutaneous T-Cell lymphoma, ductal carcinoma in situ, endometrial cancer, ependymoma, esophageal cancer, esthesioneuroblastoma, extracranial germ cell tumor, extragonadal germ cell tumor, eye cancer (including, but not limited to, intraocular melanoma and retinoblastoma), fallopian tube cancer, gallbladder cancer, gastric cancer, gastrointestinal carcinoid tumor, gastrointestinal stromal tumors, central nervous system germ cell tumors, extracranial germ cell tumors, extragonadal germ cell tumors, ovarian germ cell tumors, testicular cancer, gestational trophoblastic disease, Hairy cell leukemia, head and neck cancers, hepatocellular (liver) cancer, Langerhans cell histiocytosis, Hodgkin lymphoma, hypopharyngeal cancer, islet cell tumors, pancreatic neuroendocrine tumors, kidney (renal cell) cancer, laryngeal cancer, leukemia, lip cancer, oral cancer, lung cancer (non-small cell and small cell), lymphoma, melanoma, Merkel cell carcinoma, mesothelioma, metastatic squamous cell neck cancer, midline tract carcinoma with and without NUT gene changes, multiple endocrine neoplasia syndromes, multiple myeloma, plasma cell neoplasms, mycosis fungoides, myelodyspastic syndromes, myelodysplastic/myeloproliferative neoplasms, chronic myelogenous leukemia, nasal cancer, sinus cancer, non-Hodgkin lymphoma, pancreatic cancer, paraganglioma, paranasal sinus cancer, parathyroid cancer, penile cancer, pharyngeal cancer, pheochromocytoma, pituitary cancer, peritoneal cancer, prostate cancer, rectal cancer, Rhabdomyosarcoma, salivary gland cancer, uterine sarcoma, Sézary syndrome, skin cancer, small intestine cancer, large intestine cancer (colon cancer), soft tissue sarcoma, T-cell lymphoma, throat cancer, oropharyngeal cancer, nasopharyngeal cancer, hypopharyngeal cancer, thymoma, thymic carcinoma, thyroid cancer, transitional cell cancer of the renal pelvis and ureter, urethral cancer, uterine cancer, vaginal cancer, cervical cancer, vascular tumors and cancer, vulvar cancer, and Wilms Tumor.

As used herein, "chemotherapeutic agent" or "chemotherapeutic" refers to a therapeutic agent utilized to prevent or treat cancer.

As used herein, "control" can refer to an alternative subject or sample used in an experiment for comparison purpose and included to minimize or distinguish the effect of variables other than an independent variable.

The term "optional" or "optionally" means that the subsequent described event, circumstance or substituent may or may not occur, and that the description includes instances where the event or circumstance occurs and instances where it does not.

As used herein, "dose," "unit dose," or "dosage" can refer to physically discrete units suitable for use in a subject, each unit containing a predetermined quantity of a pharmaceutical formulation thereof calculated to produce the desired response or responses in association with its administration.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_W$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed by the term "subject".

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used interchangeably herein, the terms "sufficient" and "effective," can refer to an amount (e.g. mass, volume, dosage, concentration, and/or time period) needed to achieve one or more desired and/or stated result(s). For example, a therapeutically effective amount refers to an amount needed to achieve one or more therapeutic effects.

As used herein, "tangible medium of expression" refers to a medium that is physically tangible or accessible and is not a mere abstract thought or an unrecorded spoken word. "Tangible medium of expression" includes, but is not limited to, words on a cellulosic or plastic material, or data stored in a suitable computer readable memory form. The data can be stored on a unit device, such as a flash memory or CD-ROM or on a server that can be accessed by a user via, e.g. a web interface.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as cancer and/or indirect radiation damage. The effect can be therapeutic in terms of a partial or complete cure of a disease, condition, symptom or adverse effect attributed to the disease, disorder, or condition. The term "treatment" as used herein covers any treatment of cancer and/or indirect radiation damage, in a subject, particularly a human and/or companion animal, and can include any one or more of the following: (a) preventing the disease or damage from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values the specified components in the disclosed composition or formulation are equal to 100.

As used herein, "water-soluble", generally means at least about 10 g of a substance is soluble in 1 L of water, i.e., at neutral pH, at 25° C.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present disclosure. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the disclosure. For example, in the appended claims, any of the claimed embodiments can be used in any combination.

All patents, patent applications, published applications, and publications, databases, websites and other published materials cited herein are hereby incorporated by reference to the same extent as though each individual publication, published patent document, or patent application was specifically and individually indicated as being incorporated by reference.

Kits

Any of the compounds and/or formulations described herein can be presented as a combination kit. As used herein, the terms "combination kit" or "kit of parts" refers to the compounds, compositions, formulations, particles, cells and any additional components that are used to package, sell, market, deliver, and/or administer the combination of elements or a single element, such as the active ingredient, contained therein. Such additional components include, but are not limited to, packaging, syringes, blister packages, bottles, and the like. When one or more of the compounds, compositions, formulations, particles, cells, described herein or a combination thereof (e.g., agent(s)) contained in the kit are administered simultaneously, the combination kit can contain the active agent(s) in a single formulation, such as a pharmaceutical formulation, (e.g., a tablet, liquid preparation, dehydrated preparation, etc.) or in separate formulations. When the compounds, compositions, formulations, particles, and cells described herein or a combination thereof and/or kit components are not administered simultaneously, the combination kit can contain each agent or other component in separate pharmaceutical formulations. The separate kit components can be contained in a single package or in separate packages within the kit.

In some embodiments, the combination kit also includes instructions printed on or otherwise contained in a tangible medium of expression. The instructions can provide information regarding the content of the compounds and/or formulations, safety information regarding the content of the compounds and formulations (e.g., pharmaceutical formulations), information regarding the dosages, indications for use, and/or recommended treatment regimen(s) for the compound(s) and/or pharmaceutical formulations contained therein. In some embodiments, the instructions can provide directions and protocols for administering the compounds and/or formulations described herein to a subject in need thereof. In some embodiments, the instructions can provide one or more embodiments of the methods for administration of a pharmaceutical formulation such as any of the methods described in greater detail elsewhere herein.

The current disclosure describes the preparation of a carrier-free nanoparticle and its application. The self-assembled nanoparticle can selectively target EGFR positive tumor and inhibit its growth. Most nanoparticle based drug delivery systems are composed of a carrier and a payload. However, due to the low drug loading content, premature drug release, non-standardized carrier structure, and difficulty in predicating the fate of the carrier, only a few nanomedicines have been approved by FDA.

Erlotinib (compound OSI-774 developed by Genentech, Inc. and OSI Pharmaceuticals, Inc.; available under the trade name TARCEVA) induces dramatic clinical responses in cases of non-small cell lung cancers (NSCLCs) harboring activating mutations in the EGF receptor (EGFR) (1-3), which is targeted by these competitive inhibitors of ATP binding (4, 5). The effectiveness of this tyrosine kinase inhibitors may result both from alterations in the ATP cleft associated with these mutations, which lead to enhanced inhibition of the mutant kinase by these drugs, and from biological dependence of these cancer cells on the increased survival signals transduced by the mutant receptors, a phenomenon described as "oncogene addiction" (6, 7).

The current disclosure provides, in one aspect, a carrier-free nanoparticle based on the self-assembly of curcumin-erlotinib conjugate (EPC) for the treatment of cancer. EPC exhibits stronger cell killing, better anti-migration and anti-invasion effects for BxPC-3 pancreatic cancer cells than the combination of free curcumin and erlotinib. Furthermore, EPC nanoparticles could effectively accumulate in the tumor tissue in a xenograft tumor mouse model. Consequently, EPC effectively reduces the growth of pancreatic tumor and extended the medium survival time.

It was reported that the combination usage of erlotinib (ELT) and curcumin (CCM) could affect the drug resistance signaling pathways through decreasing the $\alpha v \beta 3$ integrin and increasing PDK4 gene expression, resulting in higher anticancer effectiveness. In spite of the better performance of the combination therapy compared to individual drugs, the aforementioned limitations of CCM are still unresolved, which restricts its applications in the biomedical field. Herein, we developed an ELT and CCM conjugated carrier-free nanoparticle to circumvent the limitations of CCM and enhance the synergistic anticancer effect of the two drugs.

Methods

Synthesis of PEG modified erlotinib (ELT-PEG)
In a 25 mL round-bottom flask equipped with a magnetic stirring bar, ELT (944 mg, 2.4 mmol), azido-PEG3-acid (466 mg, 2.0 mmol), $CuSO_4 \cdot 5H_2O$ (100 mg, 0.4 mmol), and sodium ascorbate (158 mg, 0.8 mmol) was dissolved in 10 mL mixed solvents DMF/$H_2O$/t-BuOH=2/1/2 under nitrogen atmosphere. The reaction mixture was warmed to 40° C. and stirred for 24 h. Then it was condensed and extracted with dichloromethane (DCM). The organic phase was dried over $Na_2SO_4$ and condensed in vacuum. The crude product was separated by flash column chromatography with silica gel (100 µm) using the gradient elution solvents of methanol and DCM (10/90) to afford ELT-PEG as a light-yellow oil (921 mg, 73.5%). The molecular structure of the product was confirmed by mass spectrometry (MS) and nuclear magnetic resonance spectroscopy (NMR).

Synthesis of PEG linked erlotinib-curcumin conjugate (EPC)

NHS (115 mg, 1.0 mmol) was added to a 10 mL DMF solution of mixed ELT-PEG (627 mg, 1.0 mmol) and EDC (230 mg, 1.5 mmol) stirred under nitrogen atmosphere for 30 min in a 25 mL round-bottom flask equipped with a magnetic stirring bar. After stirring at room temperature for 1 h, CCM (1.105 g, 3.0 mmol) was added into the reaction mixture and stirred at room temperature overnight. The reaction mixture was condensed under vacuum, and then extracted with $DCM/H_2O$ and washed three times with brine. The organic phase was dried by anhydrous $Na_2SO_4$, filtered, and then evaporated in vacuo. The crude product was separated by flash column chromatography with silica gel (100 μm) using the gradient elution solvents of methanol and DCM (5/95) to afford EPC as an orange solid (520 mg, 53.2%). The chemical structure of EPC was confirmed by MS and NMR results.

Preparation of EPC nanoparticle

An EPC nanoparticle (NP) was prepared by a one-step nano-precipitation method. The compound EPC was first dissolved in acetone and then added dropwise into deionized water with a syringe pump at 20 mL/h rate under vigorous stirring. Self-assembly of the NP occurred spontaneously. Acetone in the nano-formulation was removed at room temperature under vacuum. The particle size, polydispersity index (PDI), and zeta potential of the NPs were measured by dynamic light scattering (DLS, Zetasizer Nano ZS, Malvern Instruments Ltd, Malvern, UK). The morphology of the NP was observed using a Hitachi HT7800 transmission electron microscopy (TEM, Hitachi High-Technologies Corporation, Tokyo, Japan).

Critical Aggregation Concentration

Critical aggregation concentration (CAC) of EPC was determined by measuring the fluorescence emission of EPC with various concentrations in water. The fluorescence intensity of EPC NP dispersion in deionized water with a series of concentrations (from 0.5 μM to 10 μM) was measured ($\lambda ex=420$ nm, $\lambda em=530$ nm). The CAC value of EPC was calculated according to a plot of relative fluorescence intensity versus concentration.

Cell Culture

Human pancreatic cancer cells, BxPC-3, were cultured in Gibco™ DMEM supplemented with 10% FBS, 100 units/mL penicillin, and 100 μg/mL streptomycin at 37° C. in 75 mL culture flasks under a humidified atmosphere of 5% $CO_2$. Cells were sub-cultured when the cell confluency reached ~80%.

Cellular uptake

The cellular uptake of EPC was qualitatively examined by confocal laser scanning microscopy (CLSM) with BxPC-3 cells. Cells were seeded in 35 $mm^2$ Petri dish with a glass window at a density of 200,000 cells/dish for 24 h at 37° C. with 5% $CO_2$. Then cells were washed with PBS (pH 7.4) and incubated with CCM, ELT, or EPC at a concentration of 10 μM for 3 h. Cells without receiving any treatment were utilized as control. All cells were subsequently washed three times with PBS and fixed with paraformaldehyde (4% in PBS) for 10 min at room temperature. Cells were washed with PBS again for three times after the removal of paraformaldehyde, and the nuclei of cells were stained with Hoechst 33342 (final concentration 1 μg/mL) for 10 min. At last, cells were washed three times with PBS and then imaged under a confocal microscope (LSM 700, Carl-Zeiss Inc.).

Flow Cytometry

The uptake of EPC by BxPC-3 cells was further quantitatively determined by flow cytometry. Cells were seeded in 6-well plates at a density of 300,000 cells/well for 24 h at 37° C. with 5% $CO_2$. Then cells were washed with PBS (pH 7.4) and incubated with 10 μM CCM, ELT, or EPC for 3 h. Cells with no incubation were utilized as control. After that, cells were washed with PBS, trypsinized with trypsin-EDTA, and collected through centrifuging at 2000 rpm. Cells were suspended into PBS and then centrifuged for two more times. Finally, collected cells were re-suspended into PBS for analysis. Intracellular fluorescence intensity was quantified by flow cytometer (BD Accuri C6, BD Biosciences).

Cellular uptake determination

The intracellular levels of CCM and EPC were determined by fluorescence spectrometer. Cells were seeded in 6-well plates at a density of 700,000 cells/well for 24 h at 37° C. with 5% $CO_2$. Then cells were washed with PBS (pH 7.4) and incubated with 20 μM CCM or EPC for 3 h. Cells with no incubation were utilized as control. After that, cells were washed with PBS, trypsinized with trypsin-EDTA, and collected through centrifuging at 2000 rpm. Then cells were suspended in 100 μL ice-cold deionized water and ultrasonicated for 20 min at 4° C. 100 μL DMSO was added and the resulted mixture was centrifuged at 10,000 rpm for 10 min. The fluorescence emission of the supernatant was measured ($\lambda ex=420$ nm, $\lambda em=530$ nm).

Cytotoxicity Assay

The anticancer activity of the EPC NP against BxPC-3 cells was evaluated by MTT assay. Cells were seeded in 96-well plates at a density of 5,000 cells/well for 24 h prior to the test at 37° C. with 5% $CO_2$. Then cells were treated with varying concentrations of CCM, ELT, CCM+ELT, or EPC in fresh medium and further incubated for 20 h. In the control group, cells were allowed to grow without any treatment. After that, the medium was replaced with fresh medium containing MTT reagent (final concentration 1 mg/mL) and cells were further incubated for 4 h. The purple MTT crystal was dissolved with MTT stop solution and the optical density at 595 nm was recorded on a microplate reader (ELX808, Bio-Tech Instrument, Inc.).

Wound healing assay

BxPC-3 cells were seeded in a 6-well plate at the concentration of 2,000,000 cells/well. When the cell confluency reached almost 100%, the supernatant was aspirated and then the cells were scratched with a yellow pipette tip to generate the wound. After being washed with PBS, the cells were incubated with medium containing 10 μM CCM, ELT, CCM+ELT, or EPC for 24 h. The scratched areas were monitored and photographed with light microscopy.

Transwell Invasion Assay

Cell invasion assay was performed using a 24-well plate with 8 μm pore size Transwell inserts (Costar Corp., Cambridge, MA). Briefly, 50 μL Matrigel was added into each insert and solidified at 37° C. for 30 minutes to generate a thin gel layer. BxPC-3 cells treated with 10 μM CCM, ELT, CCM+ELT, or EPC in 200 μL serum-free medium were transferred into upper chambers at the concentration of 100,000 cells/well. The bottom chambers contained 600 μL complete medium with the same concentration of respective drugs. After incubation at 37° C. for 24 h, cells in the upper chamber were removed, and the invaded cells attached to the underside surface of the membrane were fixed with 4% paraformaldehyde for 30 min and then counted under a light microscope.

Cell Adhesion Assay

Cellular adhesion test was performed in a 24-well plate coated with 0.1 mg/mL Matrigel. In brief, BxPC-3 cells treated with 10 µM CCM, ELT, CCM+ELT, or EPC in 0.5 mL serum-free medium were transferred into each well at the density of 100,000 cells/well. The plate was incubated at 37° C. for 60 min, after which it was washed with PBS to remove unattached cells. Cells attached to Matrigel were fixed with methanol for 15 min and then counted in five random optical fields as determined by light microscopy.

Tumor Spheroid Assay

BxPC-3 cells were seeded in Corning® Ultra-Low Attachment 96-well plate at a density of 50,000 cells/well. Cells were incubated for 5 days to form tumor spheroids. Tumor spheroids were incubated with CCM, ELT, CCM+ELT, or EPC at a concentration of 20 µM for 6 h. Tumor spheroids without any treatment were utilized as a control. Then the tumor spheroids were washed with PBS and imaged with the confocal microscope.

To investigate the cytotoxicity that the EPC NPs exerted to the tumor spheroids, the spheroids were incubated with 20 µM CCM, ELT, CCM+ELT, or EPC for 24 h. Tumor spheroids treated with PBS were utilized as a control. The morphology change of tumor spheroids after the treatments was observed by light microscopy. To visually evaluate the cytotoxicity effect of EPC, red-emissive propidium iodide was used to stain dead cells. The tumor spheroids were stained with propidium iodide (5 µM) for 2 h and then were washed with PBS and imaged with the confocal microscope.

Animal Model

All animal experiments were conducted in accordance with NIH regulations and approved by the Institutional Animal Care and Use Committee of the University of South Carolina. In brief, 2,000,000 BxPC-3 cells suspended in 100 µL DMEM culture medium were inoculated subcutaneously to a female nude mouse (8-10 weeks old, ~20 g, Jackson Laboratories). The tumor volume was measured by a digital caliper and calculated according to the following formula: Tumor volume=0.5×(tumor length)×(tumor width)$^2$. Tumor volumes were monitored every other day. The body weight and signs of pain of the animals were observed throughout the duration of experiments.

In Vivo Biodistribution

Three weeks after the inoculation of BxPC-3 cells, the tumor-bearing mice were administered with CCM and EPC by intravenous injection at a dose of 10 mg/kg equivalent to CCM. PBS (pH 7.4) was used as a control. Mice were sacrificed after 6 h post-injection, and the organs and tumors were collected for imaging. The fluorescence was recorded ex vivo with the IVIS Lumina III whole body imaging system.

Anti-tumor efficacy

When the tumor volume of BxPC-3 tumor-bearing mice reached 100 mm$^3$, the mice were randomly assigned into five groups (n=5 for each group) and were intravenously administrated with PBS, CCM, ELT, CCM+ELT, or EPC at a dose of 10 mg kg$^{-1}$ equivalent to CCM (10.7 mg/kg equivalent to ELT) twice a week. Tumor volumes (V) and body weight of the mice were measured every other day. The relative tumor volume expressed as V/V$_0$ (V$_0$ is the tumor volume when the treatment was initiated) was used to represent the tumor size change during the treatment process. Mice were sacrificed when the tumor volume reached 2,000 mm$^3$ or tumor ulceration observed, and the organs and tumors were harvested for further analysis.

Figures

Figure 2:
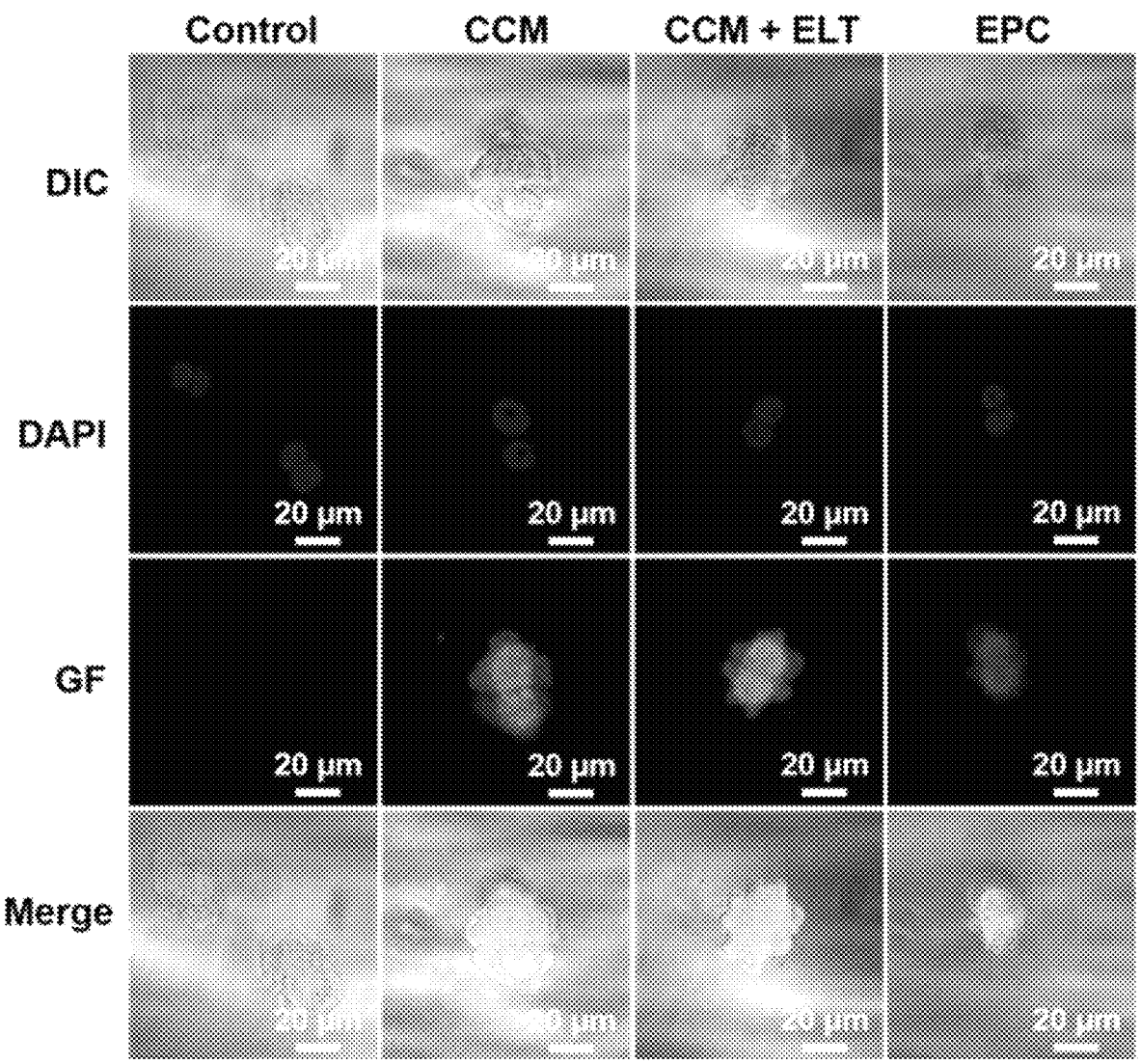
FIG. 2 shows representative CLSM images of BxPC-3 cells after various treatments for 3 h.
Figure 3:
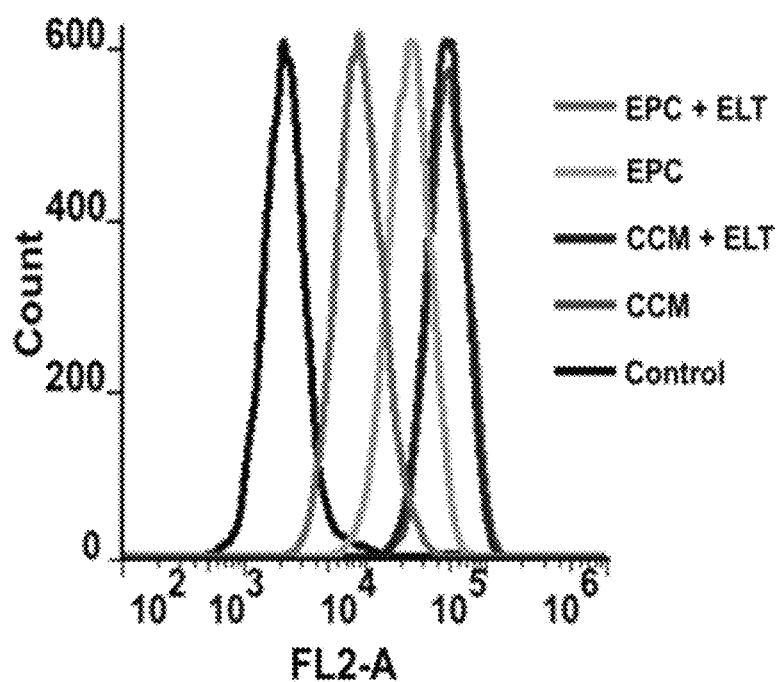
FIG. 3 shows flow cytometry analysis of BxPC-3 cells after various treatments for 3 h.
Figure 4:
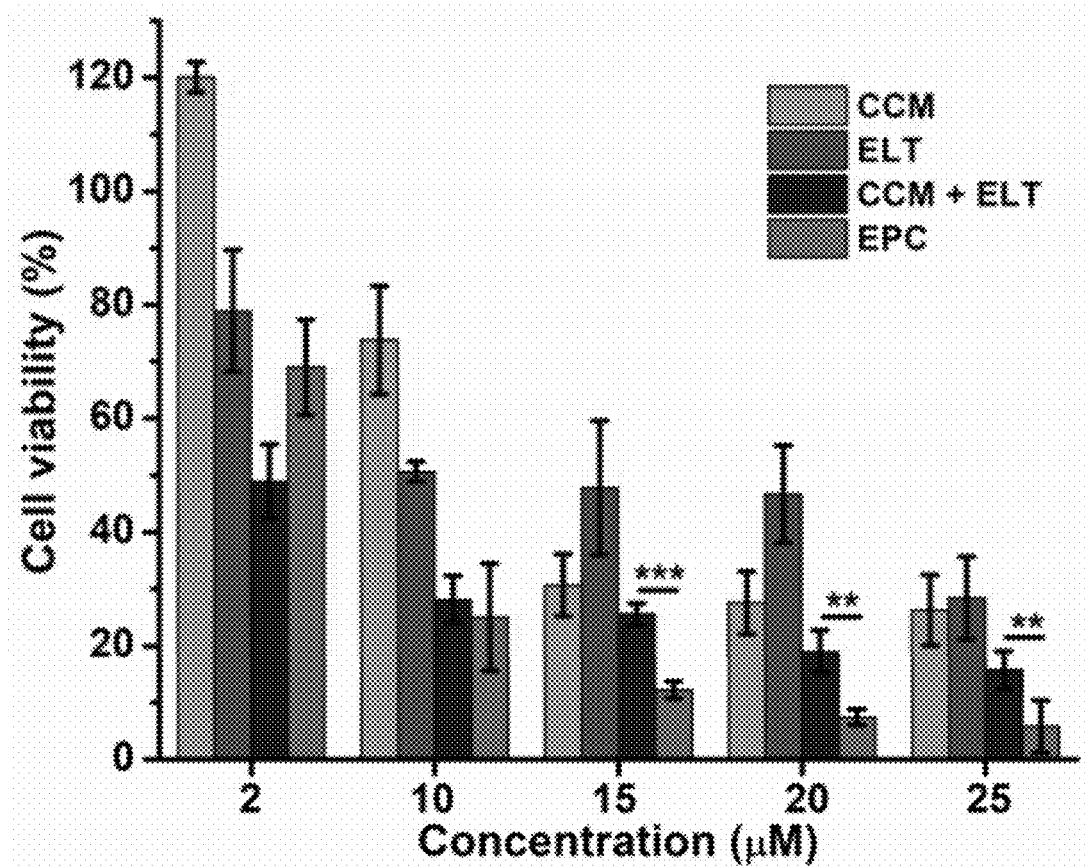
FIG. 4 shows cell viability of BxPC-3 cells after various treatments for 24 h. n=3, *P<0.05; P<0.01; and *P<0.001.
Figure 5:
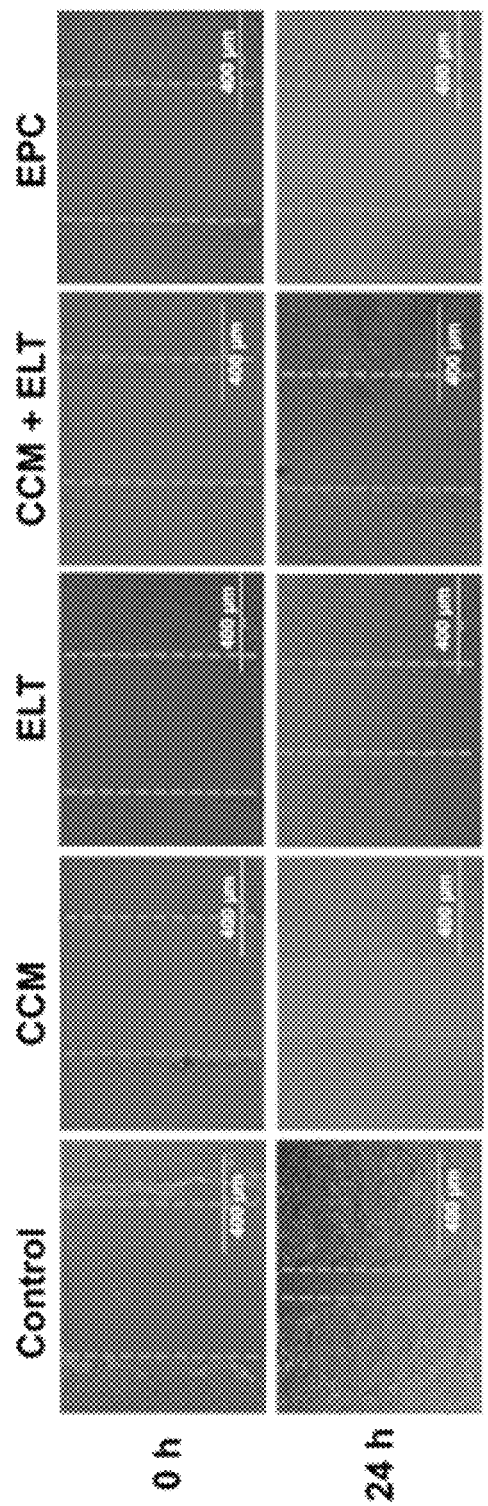
FIG. 5 shows wound healing assay of BxPC-3 cells after treatments with CCM, ELT, CCM+ELT, and EPC for 24 h.
Figure 6:
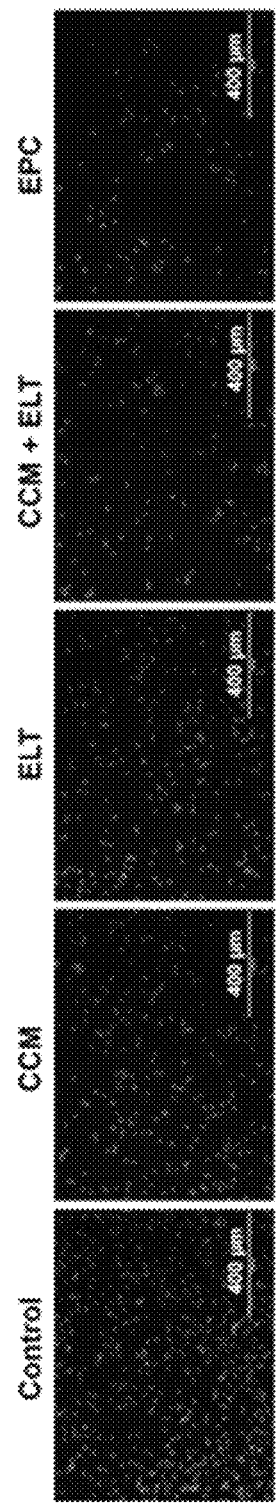
FIG. 6 shows cell adhesion assay of BxPC-3 cells after treatments with CCM, ELT, CCM+ELT, or EPC. n=3, *P<0.05; P<0.01; and *P<0.001.
Figure 7:
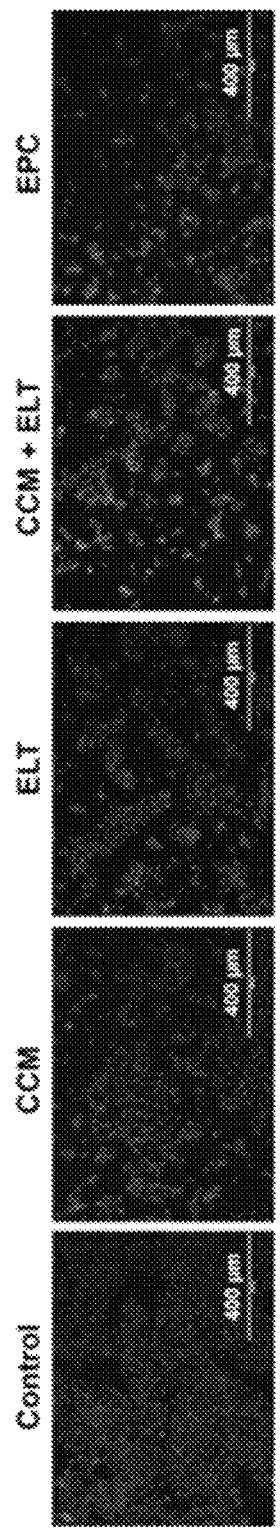
FIG. 7 shows Transwell invasion assay of BxPC-3 cells after various treatments. n=3, *P<0.05; P<0.01; and *<0.001.
Figure 8:
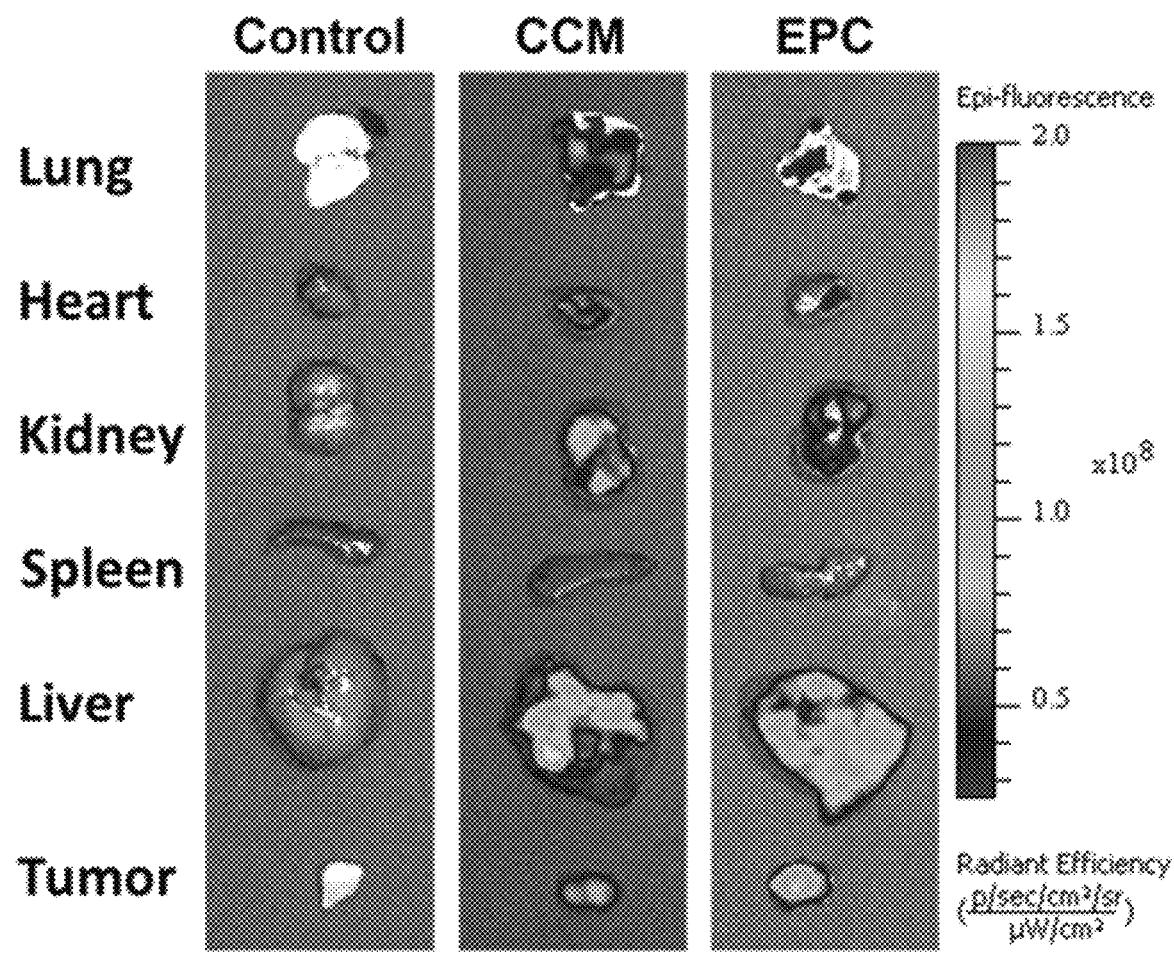
FIG. 8 shows ex vivo biodistribution of CCM and EPC nanoparticle.
Figure 9:
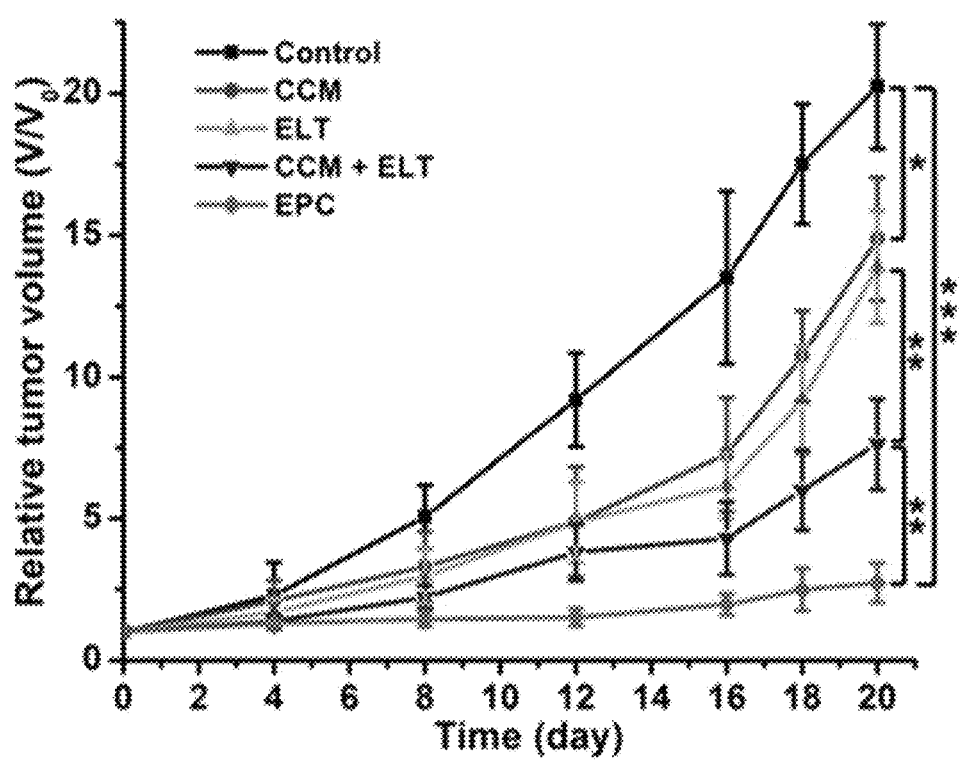
FIG. 9 shows tumor growth profiles of mice treated with different formulations. n=5, *P<0.05; P<0.01; and *<0.001.
Figure 10:
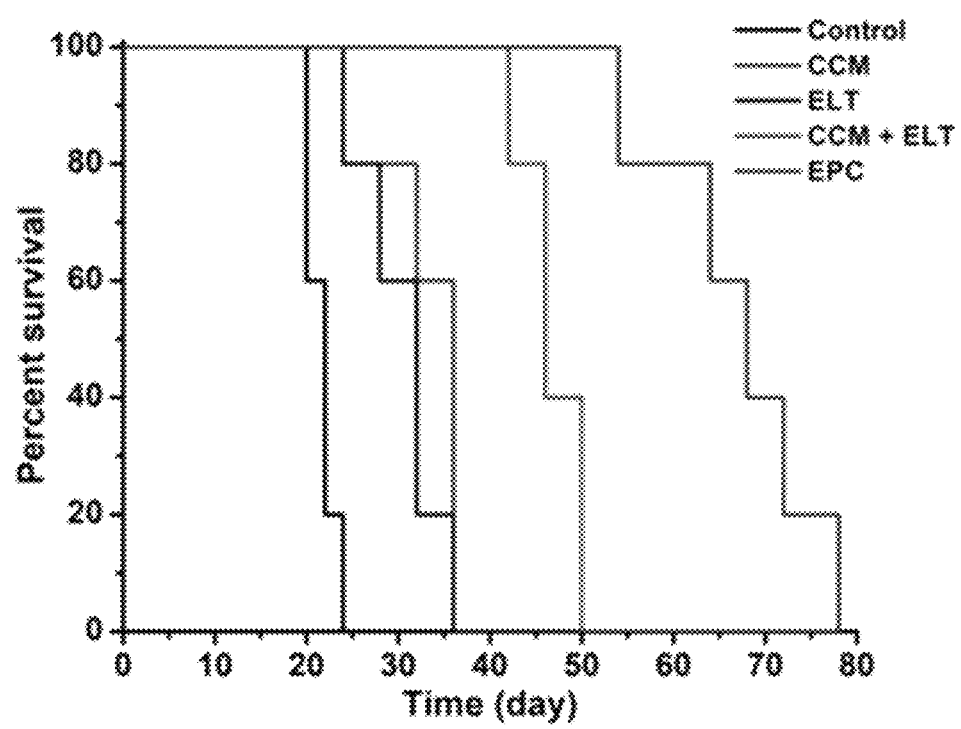
FIG. 10 shows the post-administration survival curve for mice treated with different formulations.
Figure 11:
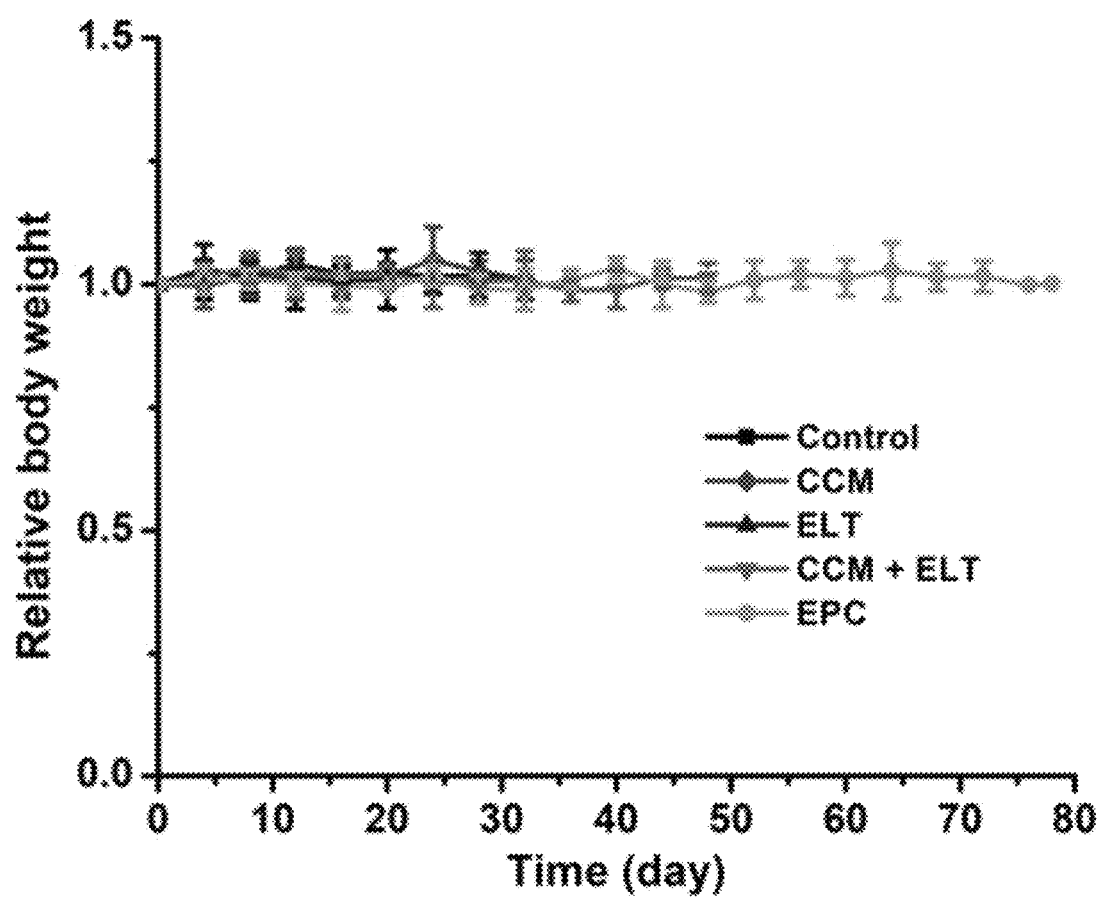
FIG. 11 shows body weight changes of mice receiving different treatments.
Figure 12:
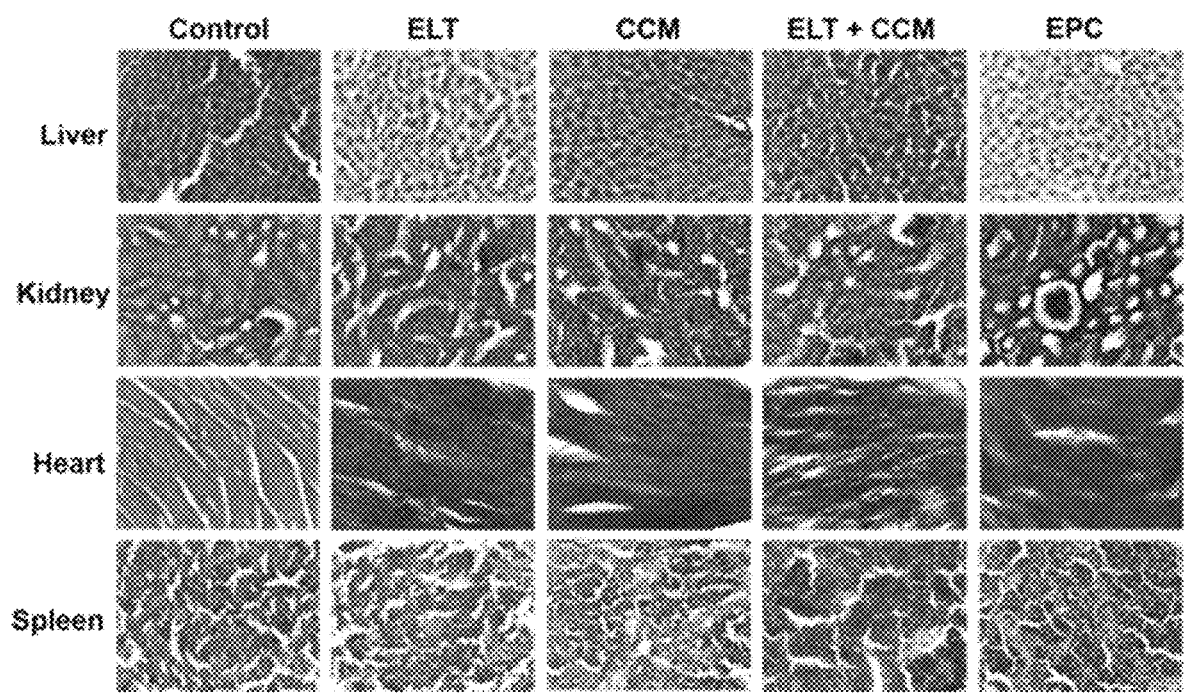
FIG. 12 shows H&E staining of major organs in different groups.

FIG. 1 shows size distribution at (A), TEM image at (B), fluorescence spectra at (C), and CMC determination at (D) of an EPC nanoparticle article of the current disclosure. FIG. 2 shows representative CLSM images of BxPC-3 cells after various treatments for 3 h. The green fluorescence (GF channel) is from CCM/EPC and the blue fluorescence (DAPI channel) is from Hoechst 33342. The scale bar is 20 µm. FIG. 3 shows flow cytometry analysis of BxPC-3 cells after various treatments for 3 h. FIG. 4 shows cell viability of BxPC-3 cells after various treatments for 24 h. n=3, *P<0.05; P<0.01; and *<0.001. FIG. 5 shows wound healing assay of BxPC-3 cells after treatments with CCM, ELT, CCM+ELT, and EPC for 24 h. FIG. 6 shows cell adhesion assay of BxPC-3 cells after treatments with CCM, ELT, CCM+ELT, or EPC. n=3, *P<0.05; P<0.01; and *<0.001. FIG. 7 shows Transwell invasion assay of BxPC-3 cells after various treatments. n=3, *P<0.05; P<0.01; and *P<0.001. FIG. 8 shows ex vivo biodistribution of CCM and EPC nanoparticle. FIG. 9 shows tumor growth profiles of mice treated with different formulations. n=5, *P<0.05; P<0.01; and *<0.001. FIG. 10 shows the post-administration survival curve for mice treated with different formulations. FIG. 11 shows body weight changes of mice receiving different treatments. FIG. 12 shows H&E staining of major organs in different groups.

```
Sequence Listings
<110> University of South Carolina

<120> Carrier-Free Curcumin Nanoparticle for EGFR Positive Cancer Therapy

<130> 2033101.0000282

<140> Unknown

<141> 2021-03-26

<150> U.S. Provisional Application No. 63/029,782

<151> 05-26-2020

<160> 1

<170> PatentIn

<210> 1

<211> 3878
```

```
<212> DNA

<213> Homo sapiens

<221> CDS

<222> 246...3875

<400> 1
cccggcgcag cgcggccgca gcagcctccg cccccgcac ggtgtgagcg cccgacgcgg      60
ccgaggcggc cggagtcccg agctagcccc ggcggccgcc gccgcccaga ccggacgaca    120
ggccacctcg tcggcgtccg cccgagtccc cgcctcgccg ccaacgccac aaccaccgcg    180
cacggccccc tgactccgtc cagtattgat cgggagagcc ggagcgagct cttcggggag    240 cagcg atg cga ccc tcc ggg acg gcc ggg gca gcg ctc ctg gcg ctg ctg    290
      Met Arg Pro Ser Gly Thr Ala Gly Ala Ala Leu Leu Ala Leu Leu
        1               5                  10                  15 gct gcg ctc tgc ccg gcg agt cgg gct ctg gag gaa aag aaa gtt tgc      338
Ala Ala Leu Cys Pro Ala Ser Arg Ala Leu Glu Glu Lys Lys Val Cys
                 20                  25                  30 caa ggc acg agt aac aag ctc acg cag ttg ggc act ttt gaa gat cat      386
Gln Gly Thr Ser Asn Lys Leu Thr Gln Leu Gly Thr Phe Glu Asp His
             35                  40                  45 ttt ctc agc ctc cag agg atg ttc aat aac tgt gag gtg gtc ctt ggg      434
Phe Leu Ser Leu Gln Arg Met Phe Asn Asn Cys Glu Val Val Leu Gly
         50                  55                  60 aat ttg gaa att acc tat gtg cag agg aat tat gat ctt tcc ttc tta      482
Asn Leu Glu Ile Thr Tyr Val Gln Arg Asn Tyr Asp Leu Ser Phe Leu
     65                  70                  75 aag acc atc cag gag gtg gct ggt tat gtc ctc att gcc ctc aac aca      530
Lys Thr Ile Gln Glu Val Ala Gly Tyr Val Leu Ile Ala Leu Asn Thr
 80                  85                  90                  95 gtg gag cga att cct ttg gaa aac ctg cag atc atc aga gga aat atg      578
Val Glu Arg Ile Pro Leu Glu Asn Leu Gln Ile Ile Arg Gly Asn Met
                 100                 105                 110 tac tac gaa aat tcc tat gcc tta gca gtc tta tct aac tat gat gca      626
Tyr Tyr Glu Asn Ser Tyr Ala Leu Ala Val Leu Ser Asn Tyr Asp Ala
             115                 120                 125 aat aaa acc gga ctg aag gag ctg ccc atg aga aat tta cag gaa atc      674
Asn Lys Thr Gly Leu Lys Glu Leu Pro Met Arg Asn Leu Gln Glu Ile
         130                 135                 140 ctg cat ggc gcc gtg cgg ttc agc aac aac cct gcc ctg tgc aac gtg      722
Leu His Gly Ala Val Arg Phe Ser Asn Asn Pro Ala Leu Cys Asn Val
     145                 150                 155 gag agc atc cag tgg cgg gac ata gtc agc agt gac ttt ctc agc aac      770
Glu Ser Ile Gln Trp Arg Asp Ile Val Ser Ser Asp Phe Leu Ser Asn
160                 165                 170                 175 atg tcg atg gac ttc cag aac cac ctg ggc agc tgc caa aag tgt gat      818
Met Ser Met Asp Phe Gln Asn His Leu Gly Ser Cys Gln Lys Cys Asp
                 180                 185                 190 cca agc tgt ccc aat ggg agc tgc tgg ggt gca gga gag gag aac tgc      866
Pro Ser Cys Pro Asn Gly Ser Cys Trp Gly Ala Gly Glu Glu Asn Cys
             195                 200                 205 cag aaa ctg acc aaa atc atc tgt gcc cag cag tgc tcc ggg cgc tgc      914
Gln Lys Leu Thr Lys Ile Ile Cys Ala Gln Gln Cys Ser Gly Arg Cys
         210                 215                 220 cgt ggc aag tcc ccc agt gac tgc tgc cac aac cag tgt gct gca ggc      962
Arg Gly Lys Ser Pro Ser Asp Cys Cys His Asn Gln Cys Ala Ala Gly
     225                 230                 235 tgc aca ggc ccc cgg gag agc gac tgc ctg gtc tgc cgc aaa ttc cga     1010
Cys Thr Gly Pro Arg Glu Ser Asp Cys Leu Val Cys Arg Lys Phe Arg
240                 245                 250                 255
```

```
                                              -continued
gac gaa gcc acg tgc aag gac acc tgc ccc cca ctc atg ctc tac aac      1058
Asp Glu Ala Thr Cys Lys Asp Thr Cys Pro Pro Leu Met Leu Tyr Asn
            260                 265                 270 ccc acc acg tac cag atg gat gtg aac ccc gag ggc aaa tac agc ttt      1106
Pro Thr Thr Tyr Gln Met Asp Val Asn Pro Glu Gly Lys Tyr Ser Phe
275                 280                 285 ggt gcc acc tgc gtg aag aag tgt ccc cgt aat tat gtg gtg aca gat      1154
Gly Ala Thr Cys Val Lys Lys Cys Pro Arg Asn Tyr Val Val Thr Asp
        290                 295                 300 cac ggc tcg tgc gtc cga gcc tgt ggg gcc gac agc tat gag atg gag      1202
His Gly Ser Cys Val Arg Ala Cys Gly Ala Asp Ser Tyr Glu Met Glu
            305                 310                 315 gaa gac ggc gtc cgc aag tgt aag aag tgc gaa ggg cct tgc cgc aaa      1250
Glu Asp Gly Val Arg Lys Cys Lys Lys Cys Glu Gly Pro Cys Arg Lys
320                 325                 330                 335 gtg tgt aac gga ata ggt att ggt gaa ttt aaa gac tca ctc tcc ata      1298
Val Cys Asn Gly Ile Gly Ile Gly Glu Phe Lys Asp Ser Leu Ser Ile
                340                 345                 350 aat gct acg aat att aaa cac ttc aaa aac tgc acc tcc atc agt ggc      1346
Asn Ala Thr Asn Ile Lys His Phe Lys Asn Cys Thr Ser Ile Ser Gly
            355                 360                 365 gat ctc cac atc ctg ccg gtg gca ttt agg ggt gac tcc ttc aca cat      1394
Asp Leu His Ile Leu Pro Val Ala Phe Arg Gly Asp Ser Phe Thr His
        370                 375                 380 act cct cct ctg gat cca cag gaa ctg gat att ctg aaa acc gta aag      1442
Thr Pro Pro Leu Asp Pro Gln Glu Leu Asp Ile Leu Lys Thr Val Lys
385                 390                 395 gaa atc aca ggg ttt ttg ctg att cag gct tgg cct gaa aac agg acg      1490
Glu Ile Thr Gly Phe Leu Leu Ile Gln Ala Trp Pro Glu Asn Arg Thr
400                 405                 410                 415 gac ctc cat gcc ttt gag aac cta gaa atc ata cgc ggc agg acc aag      1538
Asp Leu His Ala Phe Glu Asn Leu Glu Ile Ile Arg Gly Arg Thr Lys
                420                 425                 430 caa cat ggt cag ttt tct ctt gca gtc gtc agc ctg aac ata aca tcc      1586
Gln His Gly Gln Phe Ser Leu Ala Val Val Ser Leu Asn Ile Thr Ser
            435                 440                 445 ttg gga tta cgc tcc ctc aag gag ata agt gat gga gat gtg ata att      1634
Leu Gly Leu Arg Ser Leu Lys Glu Ile Ser Asp Gly Asp Val Ile Ile
        450                 455                 460 tca gga aac aaa aat ttg tgc tat gca aat aca ata aac tgg aaa aaa      1682
Ser Gly Asn Lys Asn Leu Cys Tyr Ala Asn Thr Ile Asn Trp Lys Lys
465                 470                 475 ctg ttt ggg acc tcc ggt cag aaa acc aaa att ata agc aac aga ggt      1730
Leu Phe Gly Thr Ser Gly Gln Lys Thr Lys Ile Ile Ser Asn Arg Gly
480                 485                 490                 495 gaa aac agc tgc aag gcc aca ggc cag gtc tgc cat gcc ttg tgc tcc      1778
Glu Asn Ser Cys Lys Ala Thr Gly Gln Val Cys His Ala Leu Cys Ser
                500                 505                 510

Ccc gag ggc tgc tgg ggc ccg gag ccc agg gac tgc gtc tct tgc cgg      1826
Pro Glu Gly Cys Trp Gly Pro Glu Pro Arg Asp Cys Val Ser Cys Arg
            515                 520                 525 aat gtc agc cga ggc agg gaa tgc gtg gac aag tgc aac ctt ctg gag      1874
Asn Val Ser Arg Gly Arg Glu Cys Val Asp Lys Cys Asn Leu Leu Glu
        530                 535                 540

Ggt gag cca agg gag ttt gtg gag aac tct gag tgc ata cag tgc cac      1922
Gly Glu Pro Arg Glu Phe Val Glu Asn Ser Glu Cys Ile Gln Cys His
545                 550                 555 cca gag tgc ctg cct cag gcc atg aac atc acc tgc aca gga cgg gga      1970
Pro Glu Cys Leu Pro Gln Ala Met Asn Ile Thr Cys Thr Gly Arg Gly
560                 565                 570                 575 cca gac aac tgt atc cag tgt gcc cac tac att gac ggc ccc cac tgc      2018
```

-continued

```
                Pro Asp Asn Cys Ile Gln Cys Ala His Tyr Ile Asp Gly Pro His Cys
                                580                 585                 590 gtc aag acc tgc ccg gca gga gtc atg gga gaa aac aac acc ctg gtc           2066
Val Lys Thr Cys Pro Ala Gly Val Met Gly Glu Asn Asn Thr Leu Val
            595                 600                 605 tgg aag tac gca gac gcc ggc cat gtg tgc cac ctg tgc cat cca aac           2114
Trp Lys Tyr Ala Asp Ala Gly His Val Cys His Leu Cys His Pro Asn
        610                 615                 620 tgc acc tac gga tgc act ggg cca ggt ctt gaa ggc tgt cca acg aat           2162
Cys Thr Tyr Gly Cys Thr Gly Pro Gly Leu Glu Gly Cys Pro Thr Asn
    625                 630                 635 ggg cct aag atc ccg tcc atc gcc act ggg atg gtg ggg gcc ctc ctc           2210
Gly Pro Lys Ile Pro Ser Ile Ala Thr Gly Met Val Gly Ala Leu Leu
640                 645                 650                 655 ttg ctg ctg gtg gtg gcc ctg ggg atc ggc ctc ttc atg cga agg cgc           2258
Leu Leu Leu Val Val Ala Leu Gly Ile Gly Leu Phe Met Arg Arg Arg
                660                 665                 670 cac atc gtt cgg aag cgctacg ctg cgg agg ctg ctg cag gag agg gag          2306
His Ile Val Arg Lys Arg Thr Leu Arg Arg Leu Leu Gln Glu Arg Glu
            675                 680                 685 ctt gtg gag cct ctt aca ccc agt gga gaa gct ccc aac caa gct ctc           2354
Leu Val Glu Pro Leu Thr Pro Ser Gly Glu Ala Pro Asn Gln Ala Leu
        690                 695                 700 ttg agg atc ttg aag gaa act gaa ttc aaa aag atc aaa gtg ctg ggc           2402
Leu Arg Ile Leu Lys Glu Thr Glu Phe Lys Lys Ile Lys Val Leu Gly
    705                 710                 715 tcc ggt gcg ttc ggc acg gtg tat aag gga ctc tgg atc cca gaa ggt           2450
Ser Gly Ala Phe Gly Thr Val Tyr Lys Gly Leu Trp Ile Pro Glu Gly
720                 725                 730                 735 gag aaa gtt aaa att ccc gtc gct atc aag gaa tta aga gaa gca aca           2498
Glu Lys Val Lys Ile Pro Val Ala Ile Lys Glu Leu Arg Glu Ala Thr
                740                 745                 750 tct ccg aaa gcc aac aag gaa atc ctc gat gaa gcc tac gtg atg gcc           2546
Ser Pro Lys Ala Asn Lys Glu Ile Leu Asp Glu Ala Tyr Val Met Ala
            755                 760                 765 agc gtg gac aac ccc cac gtg tgc cgc ctg ctg ggc atc tgc ctc acc           2594
Ser Val Asp Asn Pro His Val Cys Arg Leu Leu Gly Ile Cys Leu Thr
        770                 775                 780 tcc acc gtg cag ctc atc acg cag ctc atg ccc ttc ggc tgc ctc ctg           2642
Ser Thr Val Gln Leu Ile Thr Gln Leu Met Pro Phe Gly Cys Leu Leu
    785                 790                 795 gac tat gtc cgg gaa cac aaa gac aat att ggc tcc cag tac ctg ctc           2690
Asp Tyr Val Arg Glu His Lys Asp Asn Ile Gly Ser Gln Tyr Leu Leu
800                 805                 810                 815 aac tgg tgt gtg cag atc gca aag ggc atg aac tac ttg gag gac cgt           2738
Asn Trp Cys Val Gln Ile Ala Lys Gly Met Asn Tyr Leu Glu Asp Arg
                820                 825                 830 cgc ttg gtg cac cgc gac ctg gca gcc agg aac gta ctg gtg aaa aca           2786
Arg Leu Val His Arg Asp Leu Ala Ala Arg Asn Val Leu Val Lys Thr
            835                 840                 845 ccg cag cat gtc aag atc aca gat ttt ggg ctg gcc aaa ctg ctg ggt           2834
Pro Gln His Val Lys Ile Thr Asp Phe Gly Leu Ala Lys Leu Leu Gly
        850                 855                 860 gcg gaa gag aaa gaa tac cat gca gaa gga ggc aaa gtg cct atc aag           2882
Ala Glu Glu Lys Glu Tyr His Ala Glu Gly Gly Lys Val Pro Ile Lys
    865                 870                 875 tgg atg gca ttg gaa tca att tta cac aga atc tat acc cac cag agt           2930
Trp Met Ala Leu Glu Ser Ile Leu His Arg Ile Tyr Thr His Gln Ser
880                 885                 890                 895 gat gtc tgg agc tac ggg gtg acc gtt tgg gag ttg atg acc ttt gga           2978
Asp Val Trp Ser Tyr Gly Val Thr Val Trp Glu Leu Met Thr Phe Gly
```

-continued

```
tcc aag cca tat gac gga atc cct gcc agc gag atc tcc tcc atc ctg   3026
Ser Lys Pro Tyr Asp Gly Ile Pro Ala Ser Glu Ile Ser Ser Ile Leu
        915                 920                 925 gag aaa gga gaa cgc ctc cct cag cca ccc ata tgt acc atc gat gtc   3074
Glu Lys Gly Glu Arg Leu Pro Gln Pro Pro Ile Cys Thr Ile Asp Val
930                 935                 940 tac atg atc atg gtc aag tgc tgg atg ata gac gca gat agt cgc cca   3122
Tyr Met Ile Met Val Lys Cys Trp Met Ile Asp Ala Asp Ser Arg Pro
    945                 950                 955 aag ttc cgt gag ttg atc atc gaa ttc tcc aaa atg gcc cga gac ccc   3170
Lys Phe Arg Glu Leu Ile Ile Glu Phe Ser Lys Met Ala Arg Asp Pro
960                 965                 970                 975 cag cgc tac ctt gtc att cag ggg gat gaa aga atg cat ttg cca agt   3218
Gln Arg Tyr Leu Val Ile Gln Gly Asp Glu Arg Met His Leu Pro Ser
                980                 985                 990 cct aca gac tcc aac ttc tac cgt gcc ctg atg gat gaa gaa gac atg   3266
Pro Thr Asp Ser Asn Phe Tyr Arg Ala Leu Met Asp Glu Glu Asp Met
            995                 1000                1005 gac gac gtg gtg gat gcc gac gag tac ctc atc cca cag cag ggc ttc   3314
Asp Asp Val Val Asp Ala Asp Glu Tyr Leu Ile Pro Gln Gln Gly Phe
        1010                1015                1020 ttc agc agc ccc tcc acg tca cgg act ccc ctc ctg agc tct ctg agt   3362
Phe Ser Ser Pro Ser Thr Ser Arg Thr Pro Leu Leu Ser Ser Leu Ser
    1025                1030                1035 gca acc agc aac aat tcc acc gtg gct tgc att gat aga aat ggg ctg   3410
Ala Thr Ser Asn Asn Ser Thr Val Ala Cys Ile Asp Arg Asn Gly Leu
1040                1045                1050                1055 caa agc tgt ccc atc aag gaa gac agc ttc ttg cag cga tac agc tca   3458
Gln Ser Cys Pro Ile Lys Glu Asp Ser Phe Leu Gln Arg Tyr Ser Ser
                1060                1065                1070 gac ccc aca ggc gcc ttg act gag gac agc ata gac gac acc ttc ctc   3506
Asp Pro Thr Gly Ala Leu Thr Glu Asp Ser Ile Asp Asp Thr Phe Leu
            1075                1080                1085 cca gtg cct gaa tac ata aac cag tcc gtt ccc aaa agg ccc gct ggc   3554
Pro Val Pro Glu Tyr Ile Asn Gln Ser Val Pro Lys Arg Pro Ala Gly
        1090                1095                1100 tct gtg cag aat cct gtc tat cac aat cag cct ctg aac ccc gcg ccc   3602
Ser Val Gln Asn Pro Val Tyr His Asn Gln Pro Leu Asn Pro Ala Pro
    1105                1110                1115 agc aga gac cca cac tac cag gac ccc cac agc act gca gtg ggc aac   3650
Ser Arg Asp Pro His Tyr Gln Asp Pro His Ser Thr Ala Val Gly Asn
1120                1125                1130                1135 ccc gag tat ctc aac act gtc cag ccc acc tgt gtc aac agc aca ttc   3698
Pro Glu Tyr Leu Asn Thr Val Gln Pro Thr Cys Val Asn Ser Thr Phe
                1140                1145                1150 gac agc cct gcc cac tgg gcc cag aaa ggc agc cac caa att agc ctg   3746
Asp Ser Pro Ala His Trp Ala Gln Lys Gly Ser His Gln Ile Ser Leu
            1155                1160                1165 gac aac cct gac tac cag cag gac ttc ttt ccc aag gaa gcc aag cca   3794
Asp Asn Pro Asp Tyr Gln Gln Asp Phe Phe Pro Lys Glu Ala Lys Pro
        1170                1175                1180 aat ggc atc ttt aag ggc tcc aca gct gaa aat gca gaa tac cta agg   3842
Asn Gly Ile Phe Lys Gly Ser Thr Ala Glu Asn Ala Glu Tyr Leu Arg
    1185                1190                1195

Gtc gcg cca caa agc agt gaa ttt att gga gca tga                   3878
Val Ala Pro Gln Ser Ser Glu Phe Ile Gly Ala
1200                1205                1210
```

<210> 2

<211> 1210

-continued

```
<212> PRT

<213> Homo sapiens

<400> 2

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80
```

All patents, patent applications, published applications, and publications, databases, websites and other published materials referred to throughout the entire disclosure herein, unless noted otherwise, are incorporated herein by reference in their entirety.

Various modifications and variations of the described methods, pharmaceutical compositions, and kits of the disclosure will be apparent to those skilled in the art without departing from the scope and spirit of the disclosure. Although the disclosure has been described in connection with specific embodiments, it will be understood that it is capable of further modifications and that the disclosure as claimed should not be unduly limited to such specific embodiments. Indeed, various modifications of the described modes for carrying out the disclosure that are obvious to those skilled in the art are intended to be within the scope of the disclosure. This application is intended to cover any variations, uses, or adaptations of the disclosure following, in general, the principles of the disclosure and including such departures from the present disclosure come within known customary practice within the art to which the disclosure pertains and may be applied to the essential features herein before set forth.

SEQUENCE LISTING

```
<160> NUMBER OF SEQ ID NOS: 2

<210> SEQ ID NO 1
<211> LENGTH: 3879
<212> TYPE: DNA
<213> ORGANISM: Homo sapiens

<400> SEQUENCE: 1
cccggcgcag cgcggccgca gcagcctccg cccccgcac ggtgtgagcg cccgacgcgg        60
ccgaggcggc cggagtcccg agctagcccc ggcggccgcc gccgcccaga ccggacgaca       120
ggccacctcg tcggcgtccg cccgagtccc cgcctcgccg ccaacgccac aaccaccgcg       180
cacggccccc tgactccgtc cagtattgat cgggagagcc ggagcgagct cttcggggag       240
cagcgatgcg accctccggg acggccgggg cagcgctcct ggcgctgctg gctgcgctct       300
gcccggcgag tcgggctctg gaggaaaaga agtttgcca aggcacgagt aacaagctca        360
cgcagttggg cactttgaa gatcattttc tcagcctcca gaggatgttc aataactgtg        420
aggtggtcct tgggaatttg gaaattacct atgtgcagag gaattatgat ctttccttct       480
taaagaccat ccaggaggtg gctggttatg tcctcattgc cctcaacaca gtggagcgaa       540
ttcctttgga aaacctgcag atcatcagag gaaatatgta ctacgaaaat tcctatgcct       600
tagcagtctt atctaactat gatgcaaata aaaccggact gaaggagctg cccatgagaa       660
atttacagga atcctgcat ggcgccgtgc ggttcagcaa caaccctgcc ctgtgcaacg       720
tggagagcat ccagtggcgg gacatagtca gcagtgactt tctcagcaac atgtcgatgg       780
acttccagaa ccacctgggc agctgccaaa agtgtgatcc aagctgtccc aatgggagct       840
gctggggtgc aggagaggag aactgccaga aactgaccaa aatcatctgt gcccagcagt       900
```

```
gctccgggcg ctgccgtggc aagtccccca gtgactgctg ccacaaccag tgtgctgcag      960
gctgcacagg ccccccggga gcgactgcc tggtctgccg caaattccga gacgaagcca      1020
cgtgcaagga cacctgcccc ccactcatgc tctacaaccc caccacgtac cagatggatg      1080
tgaaccccga gggcaaatac agctttggtg ccacctgcgt gaagaagtgt ccccgtaatt      1140
atgtggtgac agatcacggc tcgtgcgtcc gagcctgtgg ggccgacagc tatgagatgg      1200
aggaagacgg cgtccgcaag tgtaagaagt gcgaagggcc ttgccgcaaa gtgtgtaacg      1260
gaataggtat tggtgaattt aaagactcac tctccataaa tgctacgaat attaaacact      1320
tcaaaaactg cacctccatc agtggcgatc tccacatcct gccggtggca tttaggggtg      1380
actccttcac acatactcct cctctggatc cacaggaact ggatattctg aaaaccgtaa      1440
aggaaatcac agggttttg ctgattcagg cttggcctga aacaggacg gacctccatg      1500
cctttgagaa cctagaaatc atacgcggca ggaccaagca acatggtcag ttttctcttg      1560
cagtcgtcag cctgaacata acatccttgg gattacgctc cctcaaggag ataagtgatg      1620
gagatgtgat aatttcagga acaaaaatt tgtgctatgc aaatacaata aactggaaaa      1680
aactgtttgg gacctccggt cagaaaacca aaattataag caacagaggt gaaaacagct      1740
gcaaggccac aggccaggtc tgccatgcct tgtgctcccc cgagggctgc tggggcccgg      1800
agcccaggga ctgcgtctct tgccggaatg tcagccgagg cagggaatgc gtggacaagt      1860
gcaaccttct ggagggtgag ccaagggagt ttgtggagaa ctctgagtgc atacagtgcc      1920
acccagagtg cctgcctcag gccatgaaca tcacctgcac aggacgggga ccagacaact      1980
gtatccagtg tgcccactac attgacggcc ccactgcgt caagacctgc ccggcaggag      2040
tcatgggaga aaacaacacc ctggtctgga agtacgcaga cgccggccat gtgtgccacc      2100
tgtgccatcc aaactgcacc tacgatgca ctgggccagg tcttgaaggc tgtccaacga      2160
atgggcctaa gatcccgtcc atcgccactg ggatggtggg ggccctcctc ttgctgctgg      2220
tggtggccct ggggatcggc ctcttcatgc gaaggcgcca catcgttcgg aagcgctacg      2280
ctgcggaggc tgctgcagga gagggagctt gtggagcctc ttacacccag tggaagctc      2340
cccaaccaag ctctcttgag gatcttgaag gaaactgaat tcaaaagat caaagtgctg      2400
ggctccggtg cgttcggcac ggtgtataag ggactctgga tcccagaagg tgagaaagtt      2460
aaaattcccg tcgctatcaa ggaattaaga gaagcaacat ctccgaaagc caacaaggaa      2520
atcctcgatg aagcctacgt gatggccagc gtggacaacc cccacgtgtg ccgcctgctg      2580
ggcatctgcc tcacctccac cgtgcagctc atcacgcagc tcatgcccttc cggctgcctc      2640
ctggactatg tccgggaaca caagacaat attggctccc agtacctgct caactggtgt      2700
gtgcagatcg caagggcat gaactacttg gaggaccgtc gcttggtgca ccgcgacctg      2760
gcagccagga acgtactggt gaaaacaccg cagcatgtca agatcacaga ttttgggctg      2820
gccaaactgc tgggtgcgga gagaaagaa taccatgcag aaggaggcaa agtgcctatc      2880
aagtggatgg cattggaatc aattttcac agaatctata cccaccagag tgatgtctgg      2940
agctacgggg tgaccgtttg ggagttgatg acctttggat ccaagccata tgacggaatc      3000
cctgccagcg agatctcctc catcctggag aaaggagaac gcctccctca gccacccata      3060
tgtaccatcg atgtctacat gatcatggtc aagtgctgga tgatagacgc agatagtcgc      3120
ccaaagttcc gtgagttgat catcgaattc tccaaaatgg cccgagaccc ccagcgctac      3180
cttgtcattc aggggatga aagaatgcat ttgccaagtc ctacagactc caacttctac      3240
```

-continued

```
cgtgccctga tggatgaaga agacatggac gacgtggtgg atgccgacga gtacctcatc   3300
ccacagcagg gcttcttcag cagcccctcc acgtcacgga ctcccctcct gagctctctg   3360
agtgcaacca gcaacaattc caccgtggct tgcattgata gaaatgggct gcaaagctgt   3420
cccatcaagg aagacagctt cttgcagcga tacagctcag accccacagg cgccttgact   3480
gaggacagca tagacgacac cttcctccca gtgcctgaat acataaacca gtccgttccc   3540
aaaaggcccg ctggctctgt gcagaatcct gtctatcaca atcagcctct gaaccccgcg   3600
cccagcagag acccacacta ccaggacccc cacagcactg cagtgggcaa ccccgagtat   3660
ctcaacactg tccagcccac ctgtgtcaac agcacattcg acagccctgc ccactgggcc   3720
cagaaaggca gccaccaaat tagcctggac aaccctgact accagcagga cttctttccc   3780
aaggaagcca agccaaatgg catctttaag ggctccacag ctgaaaatgc agaataccta   3840
agggtcgcgc cacaaagcag tgaatttatt ggagcatga                          3879
```

<210> SEQ ID NO 2
<211> LENGTH: 80
<212> TYPE: PRT
<213> ORGANISM: Homo sapiens

<400> SEQUENCE: 2

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80
```

What is claimed is:

1. A method for preparing a carrier-free nanoparticle for tumor growth inhibition comprising:
   synthesizing PEG modified erlotinib;
   conjugating the PEG modified erlotinib with curcumin to form an erlotinib-curcumin conjugate;
   dissolving the erlotinib-curcumin conjugate in acetone to form a solution; and
   adding the solution dropwise to deionized water to self-assemble at least one nanoparticle.

* * * * *